United States Patent
Tang et al.

(10) Patent No.: US 11,635,429 B2
(45) Date of Patent: Apr. 25, 2023

(54) IMMUNOCHROMATOGRAPHY TEST STRIP FOR DETECTING POLLUTION OF DIACETOXYSCIRPENOL, PREPARATION METHOD THEREFOR, AND APPLICATION THEREOF

(71) Applicant: OIL CROPS RESEARCH INSTITUTE, CHINESE ACADEMY OF AGRICULTURAL SCIENCES, Hubei (CN)

(72) In coated with a nanogold-labeled anti-diacetoxyscirpenol monoclonal antibody; and the anti-diacetoxyscirpenol monoclonal antibody is secreted by a hybridoma cell strain DAS5G11E7 with the preservation number of CCTCC NO.C201881.

10 Claims, 3 Drawing Sheets

Specification includes a Sequence Listing.

(56) References Cited

FOREIGN PATENT DOCUMENTS

| CN | 103278630 | 9/2013 |
|----|-----------|--------|
| CN | 103792365 | 5/2014 |
| CN | 108226483 | 6/2018 |
| CN | 109557305 | 4/2019 |
| CN | 110389222 | 10/2019 |
| CN | 110806476 | 2/2020 |

OTHER PUBLICATIONS

Josef Urban Pauly et al., "Production and Characterization of a Monoclonal Antibody to the Trichothecene Mycotoxin Diacetoxyscirpenol," Biol. Chem. Hoppe-Seyler, vol. 369, Jun. 1988, pp. 487-492.

"Office Action of China Counterpart Application" with English translation thereof, dated Mar. 2, 2021, p. 1-p. 19.

"Notification to Grant Patent Right of China Counterpart Application" with English translation thereof, dated Sep. 1, 2021, p. 1-p. 3.

"International Search Report (Form PCT/ISA/210) of PCT/CN2020/129072," dated May 17, 2021, with English translation thereof, pp. 1-8.

* cited by examiner

FIG. 4

SEQUENCE LISTING

<160> NUMBER OF SEQ ID NOS: 4

<210> SEQ ID NO 1
<211> LENGTH: 351
<212> TYPE: DNA
<213> ORGANISM: Mice

<400> SEQUENCE: 1

```
gaagtgcaac tggtggagtc tgggggagac ttagtgaagc ctggagggtc cctgaaactc      60
tcctgttcag cctccggatt cactttcaat tactatggca tgtcttgggt tcgccagact     120
ccagacaacc tcctggagtg ggtcgcaggc attagtagtg gtggttctta cacctattat     180
tctgacagtg tgaagggacg attcaccatc tccagagaca gtgccacgaa caccctgtac     240
ctgcaaatga ccagtctgaa gtctcaagac acagccatgt attattgtat tagactcccg     300
tttgggtcta tggactattg gggtcaagga accgcagtca ccgtctcctc a              351

<210> SEQ ID NO 2
<211> LENGTH: 324
<212> TYPE: DNA
<213> ORGANISM: Mice

<400> SEQUENCE: 2
caggctgttg tgactcagga acctgcactc accacatcac ctggtgaaac agtcacactc      60
acttgtcgct caagtactgg ggctgtaaca actggtaatt atgtcaactg gtccaagag     120 aaaccagatc atttattcag tggtctaata ggtaatacca ataaccgagc tccaggtgtt     180
cctgccagat tctcaggctc cctgattgga gacaaggctg ccctcaccat cacagggaca     240
cagactgagg atgaggcaat atatttctgt gctctatggt acaccgacca tttggtgttc     300
ggtggaggaa ccaaattgac tgtc                                            324

<210> SEQ ID NO 3
<211> LENGTH: 117
<212> TYPE: PRT
<213> ORGANISM: Mice

<400> SEQUENCE: 3

Glu Val Gln Leu Val Glu Ser Gly Gly Asp Leu Val Lys Pro Gly Gly
1               5                  10                  15

Ser Leu Lys Leu Ser Cys Ser Ala Ser Gly Phe Thr Phe Asn Tyr Tyr
            20                  25                  30

Gly Met Ser Trp Val Arg Gln Thr Pro Asp Asn Leu Leu Glu Trp Val
        35                  40                  45

Ala Gly Ile Ser Ser Gly Gly Ser Tyr Thr Tyr Tyr Ser Asp Ser Val
    50                  55                  60

Lys Gly Arg Phe Thr Ile Ser Arg Asp Ser Ala Thr Asn Thr Leu Tyr
65                  70                  75                  80

Leu Gln Met Thr Ser Leu Lys Ser Gln Asp Thr Ala Met Tyr Tyr Cys
                85                  90                  95

Ile Arg Leu Pro Phe Gly Ser Met Asp Tyr Trp Gly Gln Gly Thr Ala
            100                 105                 110

Val Thr Val Ser Ser
        115

<210> SEQ ID NO 4
<211> LENGTH: 108
<212> TYPE: PRT
<213> ORGANISM: Mice

<400> SEQUENCE: 4

Gln Ala Val Val Thr Gln Glu Pro Ala Thr Thr Ser Pro Gly Glu
1               5                  10                  15

Thr Val Thr Leu Thr Cys Arg Ser Ser Thr Gly Ala Val Thr Thr Gly
            20                  25                  30
```

```
Asn Tyr Val Asn Trp Val Gln Glu Lys Pro Asp His Leu Phe Ser Gly
        35              40              45
Leu Ile Gly Asn Thr Asn Asn Arg Ala Pro Gly Val Pro Ala Arg Phe
        50              55              60
Ser Gly Ser Leu Ile Gly Asp Lys Ala Ala Leu Thr Ile Thr Gly Thr
65              70              75              80
Gln Thr Glu Asp Glu Ala Ile Tyr Phe Cys Ala Leu Trp Tyr Thr Asp
                85              90              95
His Leu Val Phe Gly Gly Gly Thr Lys Leu Thr Val
            100             105
```

IMMUNOCHROMATOGRAPHY TEST STRIP FOR DETECTING POLLUTION OF DIACETOXYSCIRPENOL, PREPARATION METHOD THEREFOR, AND APPLICATION THEREOF This is a 371 application of the International PCT application serial no. PCT/CN2020/129072, filed on Nov. 16, 2020, which claims the priority benefits of China Application No. 201911121620.X, filed on Nov. 15, 2019. The entirety of each of the above-mentioned patent applications is hereby incorporated by reference herein and made a part of this specification.

BACKGROUND

Technical Field

The present disclosure relates to a mycotoxin immunochromatography test strip, in particular to an immunochromatography test strip for detecting pollution of diacetoxyscirpenol, a preparation method therefor, and application thereof.

Description of Related Art

Mycotoxins are toxic secondary metabolites generated in a growth process of fungi. More than 400 species of mycotoxins are discovered so far. Among them, trichothecene is a toxin with relatively high pollution level and relatively large harm in fusarium toxins and has the characteristics of strong toxicity, wide pollution range, and high frequency. Trichothecene mycotoxins are classified into four types from A to D, where type A and type B have relatively large harm. Diacetoxyscirpenol in the type A has relatively strong acute toxicity, and has LD50 of 0.75 mg/kg for rats. In addition, diacetoxyscirpenol is relatively strong in thermal stability. The toxin cannot be damaged by general cooking methods and is liable to enter a food chain to harm human health. Clinical manifestations after poisoning include severe dermatitis, nausea, vomiting, bloody diarrhea, bone marrow hematopoietic system damage, nervous system disorders, anorexia, and death. As people have increasingly higher requirements for food quality safety, a safety consumption requirement of people should be met to a greater extent by enhancing monitoring of diacetoxyscirpenol in grains, developing accurate and efficient detection technologies, especially rapid detection technologies, shortening analysis time, and improving food safety in China.

Existing methods for detecting diacetoxyscirpenol mainly are instrumental methods, including high performance liquid chromatography, liquid chromatography-mass spectrometry, and tandem mass spectrometry. These methods are high in detection sensitivity and accuracy, but preprocessing steps are complex, consumed time is relatively high, specific experimental environments and professional testers are needed, so that the methods are suitable for detection in a laboratory. Immunoassay has been rapidly developed in recent years due to the advantages of strong specificity, high sensitivity, low cost, adaptability to field batch detection, and the like. The immunochromatography test strip based on specific binding reactions of colloidal gold labelled antibodies and antigens has been widely used in qualitative, online and rapid detection of trace compounds such as mycotoxins in recent years because of detection results visible to the naked eye, low detection cost and short analysis time. However, a colloidal gold immunochromatography test strip for detecting diacetoxyscirpenol has not been seen in the market at present. In recent years, several articles have reported that pollution of diacetoxyscirpenol in grain tends to increase. Therefore, there is an urgent need of a detection technology capable of rapidly detecting pollution of diacetoxyscirpenol on site, so as to guarantee food safety in China.

SUMMARY

To solve the problem, the present disclosure provides an immunochromatography test strip for detecting pollution of diacetoxyscirpenol, a preparation method therefor, and application thereof. The immunochromatography test strip can be used to detect a quantity of diacetoxyscirpenol contained in a sample, and has the characteristics of high sensitivity and simple and rapid operation.

To solve the foregoing technical problem, the technical solution adopted by the present disclosure is as follows:

an immunochromatography test strip for detecting pollution of diacetoxyscirpenol includes a bottom plate, where a water absorption pad, a detection pad, a gold-labeled pad, and a sample pad are sequentially attached to one side of the bottom plate from top to bottom, adjacent pads are connected in an overlapping manner at a joint, the detection pad uses a nitrocellulose membrane as a base pad, a quality control line and a detection line are transversely arranged on the nitrocellulose membrane, the quality control line is coated with a rabbit antimouse polyclonal antibody, the detection line is located below the quality control line, and the detection line is coated with a diacetoxyscirpenol-ovalbumin conjugate (DAS-OVA); the gold-labeled pad is transversely spray-coated with a nanogold-labeled anti-diacetoxyscirpenol monoclonal antibody; the anti-diacetoxyscirpenol monoclonal antibody is secreted by a hybridoma cell strain DAS5G11E7 with the preservation number of CCTCC NO.C201881; and this hybridoma cell strain DAS5G11E7 has already been preserved on Apr. 3, 2018 in China Center For Type Culture Collection (CCTCC), the preservation address is Wuhan University, Wuhan, China, and the preservation number is CCTCC NO.C201881.

According to the foregoing solution, the water absorption pad is 16 mm to 18 mm in length and 3 mm to 4 mm in width, the detection pad is 18 mm to 30 mm in length and 3 mm to 4 mm in width, the gold-labeled pad is 10 mm to 12 mm in length and 3 mm to 4 mm in width, the sample pad is 12 mm to 15 mm in length and 3 mm to 4 mm in width, and an overlapping length of adjacent pads is 1 mm to 3 mm.

According to the foregoing solution, the water absorption pad is water absorption paper.

According to the foregoing solution, a distance between the detection line and an upper edge of the nitrocellulose membrane is 15 mm to 20 mm, and a distance between the detection line and the quality control line is 5 mm to 7 mm.

According to the foregoing solution, a coating quantity of the diacetoxyscirpenol-ovalbumin conjugate (DAS-OVA) required for each centimeter of the detection line is 100 ng to 300 ng, and a coating quantity of the rabbit antimouse polyclonal antibody required for each centimeter of the quality control line is 50 ng to 200 ng.

According to the foregoing solution, a particle size of nanogold used in the gold-labeled pad is 15 nm to 20 nm, and a dosage of the nanogold-labeled anti-diacetoxyscirpenol monoclonal antibody required for each centimeter of spray-coating length on the gold-labeled pad is 100 ng to 200 ng.

A preparation method for the immunochromatography test strip for detecting pollution of diacetoxyscirpenol as described above includes the following steps.

(1) Preparation of the Water Absorption Pad cutting water absorption paper to obtain the water absorption pad;

(2) Preparation of the Detection Pad coating of the detection line:

preparing a coating solution with a concentration of 0.25 mg/mL to 0.5 mg/mL from the diacetoxyscirpenol-ovalbumin conjugate (DAS-OVA) by using a coating buffer solution, coating the nitrocellulose membrane with the coating solution in a spot-spray manner to obtain the detection line, and then drying at 37° C. to 40° C. for 30 min to 60 min; where a coating quantity of the diacetoxyscirpenol-ovalbumin conjugate (DAS-OVA) required for each centimeter of the detection line coated with the diacetoxyscirpenol-ovalbumin conjugate (DAS-OVA) is 100 ng to 300 ng, and a distance between the detection line and an upper edge of the nitrocellulose membrane is 15 mm to 20 mm;

coating of the quality control line:

preparing a coating solution with a concentration of 0.2 mg/mL to 0.4 mg/mL from the rabbit antimouse polyclonal antibody by using a coating buffer solution; transversely coating the nitrocellulose membrane with the coating solution in a position 5 mm to 7 mm away from the detection line close to the quality control line in a spot-spray manner to obtain the quality control line, where a coating quantity of the rabbit antimouse polyclonal antibody required for each centimeter of the quality control line is 50 ng to 200 ng; and then, drying is performed at 37° C. to 40° C. for 1 h to 2 h;

(3) Preparation of the Sample Pad:

putting a fiberglass membrane into a blocking solution to be soaked, taking out the soaked fiberglass membrane, and drying at 37° C. to 40° C. for 6 h to 10 h to obtain the sample pad, and then, preserving the sample pad in a dryer at room temperature;

(4) Preparation of the Gold-Labeled Pad putting a fiberglass membrane into a blocking solution to be soaked, taking out the soaked fiberglass membrane, and drying at 37° C. to 40° C. for 6 h to 10 h; transversely spray-coating the dried fiberglass membrane with a nanogold-labeled anti-diacetoxyscirpenol monoclonal antibody solution in a spot-spray manner, where a dosage of the nanogold-labeled anti-diacetoxyscirpenol monoclonal antibody required for each centimeter of spray-coating length is 100 ng to 200 ng; and then, vacuum freeze-drying for 2 h to 4 h, and preserving in a dryer at room temperature; and the anti-diacetoxyscirpenol monoclonal antibody is secreted by a hybridoma cell strain DAS5G11E7 with the preservation number of CCTCC NO.C201881; and (5) Assembling of the Test Strip sequentially attaching the water absorption pad, the detection pad, the gold-labeled pad, and the sample pad to one side of a bottom plate from top to bottom to obtain the immunochromatography test strip for detecting pollution of diacetoxyscirpenol, where adjacent pads are connected in an overlapping manner at a joint, and an overlapping length is 1 mm to 3 mm.

According to the foregoing solution, the coating buffer solution includes in each 10 mL: 0.08 g of sodium chloride, 0.002 g of potassium chloride, 0.002 g of monopotassium phosphate, 0.1 g to 0.2 g of ovalbumin, and 0.029 g of sodium phosphate dibasic dodecahydrate.

According to the foregoing solution, the blocking solution used in the step (3) and the step (4) includes in each 100 mL: 2 g to 5 g of sucrose, 0.8 g of sodium chloride, 0.02 g of potassium chloride, 0.02 g to 0.05 g of sodium azide, 0.02 g of monopotassium phosphate, 1 g to 2 g of bovine serum albumin, and 0.29 g of sodium phosphate dibasic dodecahydrate.

According to the foregoing solution, the nanogold-labeled anti-diacetoxyscirpenol monoclonal antibody is prepared by using an unsaturated labeling method, specifically including: taking 50.0 mL of a commercially available nanogold solution with a mass concentration of 0.01%, adjusting a pH value by using 0.6 mL of a 0.1 mol/L potassium carbonate aqueous solution, slowly adding 2.0 mL of a 0.1 mg/mL anti-diacetoxyscirpenol monoclonal antibody aqueous solution while stirring, and continuing conducting stirring for 30 min; adding a bovine serum albumin aqueous solution with a mass concentration of 10% until a final mass concentration of bovine serum albumin is 1%, and continuing conducting stirring for 30 min; standing at 4° C. for 2 h, centrifuging at 1500 r/min for 15 min, taking the obtained supernate, and discarding the obtained precipitate; centrifuging the supernate at 12000 r/min for 30 min, discarding the obtained supernate, and adding 40.0 mL of label washing preserving fluid; and then, centrifuging at 12000 r/min for 30 min, discarding the obtained supernate, resuspending the obtained precipitate by using label washing preserving fluid to obtain 5.0 mL of a concentrate, and placing the obtained concentrate in a refrigerator at 4° C. for standby application;

where the 0.1 mol/L potassium carbonate aqueous solution is prepared by dissolving 13.8 g of potassium carbonate in pure water until a constant volume of 1000 mL and filtering by using a 0.22 μm filter membrane, and the label washing preserving fluid is prepared from 0.2 g of sodium azide, 0.1235 g of boric acid, 2.0 g of polyethylene glycol-20000 and pure water in a constant volume of 1000 mL by filtering by using a 0.22 μm filter membrane.

Application of the immunochromatography test strip for detecting pollution of diacetoxyscirpenol as described above includes: weighing a to-be-tested ground sample, adding a methanol aqueous solution with a volume concentration of 60% to 80%, evenly mixing, ultrasonically extracting in a water bath at 50° C. to 60° C. for 5 min to 10 min, standing for 5 min to 10 min, diluting the obtained supernate, namely the obtained extract with water so that a final volume concentration of methanol in diluted liquid is 20% to 30% to obtain a to-be-tested sample solution, taking 80 μL to 150 μL of the to-be-tested sample solution as a detected solution to be dropwise added onto the sample pad of the immunochromatography test strip for detecting pollution of diacetoxyscirpenol for detection as a detection test strip, taking an equal volume of methanol aqueous solution with a consistent methanol concentration as a negative control solution to be dropwise added onto a sample pad of another immunochromatography test strip for detecting pollution of diacetoxyscirpenol as a control test strip, and performing developing contrast on the detection test strip and the control test strip 15 min to 20 min later, wherein when color of the detection line coated with the diacetoxyscirpenol-ovalbumin conjugate on the detection test strip approaches color of the corresponding detection line on the control test strip, it is indicated that a quantity of diacetoxyscirpenol contained in the to-be-tested sample solution is less than 5 ng/mL; when the color of the detection line coated with the diacetoxyscirpenol-ovalbumin conjugate on the detection test strip is lighter than the color of the corresponding detection line on the control test strip, it is indicated that a quantity of diacetoxyscirpenol contained in the to-be-tested sample solution is equal to or higher than 5 ng/mL and less than 100 ng/mL; when color is not developed, it is indicated that a quality of diacetoxyscirpenol contained in the to-be-tested sample solution is equal to or higher than 100 ng/mL; and when color is not developed on the quality control line, the test strip is determined as invalid no matter whether color is developed on the detection line of the detection test strip; and finally, a quantity of diacetoxyscirpenol contained in the to-be-tested sample is obtained through conversion.

For the application of the immunochromatography test strip provided in the present disclosure to detecting pollution of diacetoxyscirpenol, a working principle includes: when the to-be-tested sample solution is added to the sample pad at a lower end of the test strip, the to-be-tested sample solution moves toward the water absorption pad along the test strip under a capillary action, and when the to-be-tested sample solution moves to the gold-labeled pad, the nano-gold-labeled anti-diacetoxyscirpenol monoclonal antibody is dissolved. When the sample contains diacetoxyscirpenol, diacetoxyscirpenol binds to the nanogold-labeled anti-diacetoxyscirpenol monoclonal antibody on the gold-labeled pad to jointly swim upward. When the to-be-tested sample solution reaches the detection line with a fixed diacetoxyscirpenol-ovalbumin conjugate antigen, the antigen with which the detection line is coated competes with diacetoxyscirpenol to bind to limited antigen binding sites on the nanogold-labeled anti-diacetoxyscirpenol monoclonal antibody. The higher the quantity of diacetoxyscirpenol contained in the sample is, the fewer the nanogold-labeled anti-diacetoxyscirpenol monoclonal antibody that can bind to the antigen on the detection line is, and the lighter the color of developing stripes formed on the detecting line is. When a quantity of the corresponding nanogold-labeled antibody that binds to the antigen on the detection line is less than a certain value, no red stripes appear on the detection line. No matter whether the sample contains such mycotoxin, the nanogold-labeled anti-mycotoxin antibody or a bound substance of the nanogold-labeled anti-mycotoxin antibody and the mycotoxin that is not intercepted by the antigen on the detection line continues to move to the quality control line and binds to the rabbit antimouse polyclonal antibody on the quality control line to be enriched for developing. In view of the above, developing contrast is performed on color of the detection line coated with the diacetoxyscirpenol-ovalbumin conjugate on the detection test strip and color of the corresponding detection line on the control test strip, so that a pollution situation of this mycotoxin, namely the diacetoxyscirpenol in the sample can be obtained.

The present disclosure has the beneficial effects:

(1) Pollution of diacetoxyscirpenol is detected by one step. The immunochromatography test strip for detecting pollution of diacetoxyscirpenol provided in the present disclosure can rapidly detect this mycotoxin, namely the diacetoxyscirpenol.

(2) Sensitivity is high. A low of detection of the immunochromatography test strip provided in the present disclosure for diacetoxyscirpenol in a detected solution is 5 ng/mL.

(3) Operation is simple. For sample preprocessing, only after adding a methanol water extract to a sample, ultrasonically extracting for 5 min to 10 min, then standing for 5 min to 10 min, and taking supernate to be diluted, detection can be performed. The whole sample preprocessing is simple and rapid.

BRIEF DESCRIPTION OF THE DRAWINGS

FIG. 1 is a front view of an immunochromatography test strip for detecting pollution of diacetoxyscirpenol according to the present disclosure;

FIG. 2 is a diagram illustrating determination of results according to Embodiment 2;

In the figure: 1 Paper board; 2 Water absorption pad; 3 Detection pad; 4 Quality control line; 5 Detection line; 6 Gold-labeled pad; and 7 Sample pad;

FIG. 3 illustrates affinity measurement data of a diacetoxyscirpenol monoclonal antibody provided by the present disclosure; and (a) of FIG. 4 illustrates results of cross reactions between a diacetoxyscirpenol monoclonal antibody and other mycotoxins provided by the present disclosure; and (b) of FIG. 4 illustrates a diacetoxyscirpenol enzyme linked immunoassay standard curve constructed by a diacetoxyscirpenol monoclonal antibody provided by the present disclosure.

DESCRIPTION OF THE EMBODIMENTS

Embodiment 1: Obtaining of Anti-Diacetoxyscirpenol Monoclonal Antibody

An anti-diacetoxyscirpenol monoclonal antibody was secreted by a hybridoma cell strain DAS5G11E7 with the preservation number of CCTCC NO.C201881. A preparation method included:

injecting the hybridoma cell strain DAS5G11E7 into BALB/c mice preprocessed by using a Freund's incomplete adjuvant, collecting ascites of the mice, and purifying the antibody by using a caprylic acid-ammonium sulfate method. Specific operation included: filtering the ascites of the mice by using double-layer filter paper, centrifuging at 4° C. and 12000 r/min for 15 min or above, sucking supernate, mixing the obtained ascites supernate with 4 times volume of an acetate buffer solution, slowly adding n-caprylic acid while stirring, with 30 μL to 35 μL of n-caprylic acid required for each mL of ascites, mixing at room temperature for 30 min to 60 min, and standing at 4° C. for 2 h or above; centrifuging at 12000 r/min and 4° C. for 30 min or above, discarding the obtained precipitate, filtering the resulting supernate by using double-layer filter paper, adding a phosphate buffer solution with a molar concentration of 0.1 mol/L and a pH of 7.4, with a volume being 1/10 that of the obtained filtrate, adjusting the pH of the mixed solution to 7.4 by using a 2 mol/L sodium hydroxide solution, slowly adding ammonium sulfate in an ice bath to reach an ammonium sulfate final concentration of 0.277 g/mL, standing at 4° C. for 2 h or above, then centrifuging at 12000 r/min and 4° C. for 30 min or above, discarding supernate, resuspending the resulting precipitate by using a phosphate buffer solution with a molar concentration of 0.01 mol/L and a pH of 7.4, with a volume being 1/10 that of the original ascites, filling a dialysis bag, dialyzing by using 0.01 mol/L PBS for 2 d, then dialyzing by using PB for 2 d, taking a protein solution out of the dialysis bag, centrifuging, collecting supernate, discarding the obtained precipitate, prefreezing at −70° C., and putting the prefrozen material into a freeze dryer for freeze-drying; and collecting freeze-dried powder, namely the purified anti-diacetoxyscirpenol monoclonal antibody.

The acetate buffer solution was prepared from 0.29 g of sodium acetate, 0.141 mL of acetic acid, and water that was added until a constant volume of 100 mL; the 0.01 mol/L phosphate buffer solution was prepared from 0.8 g of sodium chloride, 0.29 g of sodium phosphate dibasic dodecahydrate, 0.02 g of potassium chloride, and 0.02 g of monopotassium phosphate, and water that was added until a constant volume of 100 mL; and the 0.1 mol/L phosphate buffer solution was prepared from 8 g of sodium chloride, 2.9 g of sodium phosphate dibasic dodecahydrate, 0.2 g of potassium chloride, 0.2 g of monopotassium phosphate, and water that was added until a constant volume of 100 mL.

A subtype of the anti-diacetoxyscirpenol monoclonal antibody secreted by the hybridoma cell strain DAS5G11E7 was identified to be IgG2b by using a commercially available subtype identification kit.

It was measured by using a conventional non-competitive enzyme-linked immunosorbent assay (ELISA) that a valence of the antibody obtained from the mouse ascites by purifying might reach $3

TABLE 1-continued

Cross reaction of DAS5G11E7 with other toxins

| Name of toxin | Structure | IC50 | Cross reactivity |
|---|---|---|---|
| FB$_1$ | | >100,000 | <0.01% |
| OTA | | >100,000 | <0.01% |

Figure 1:
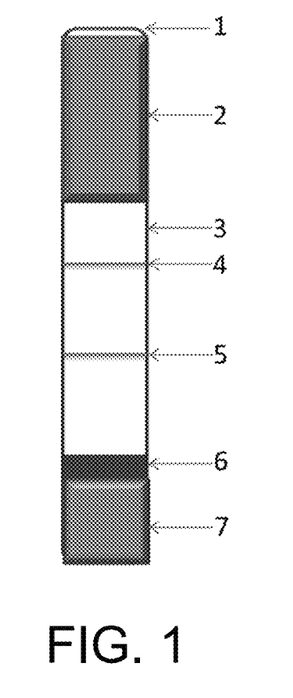
Figure 2:
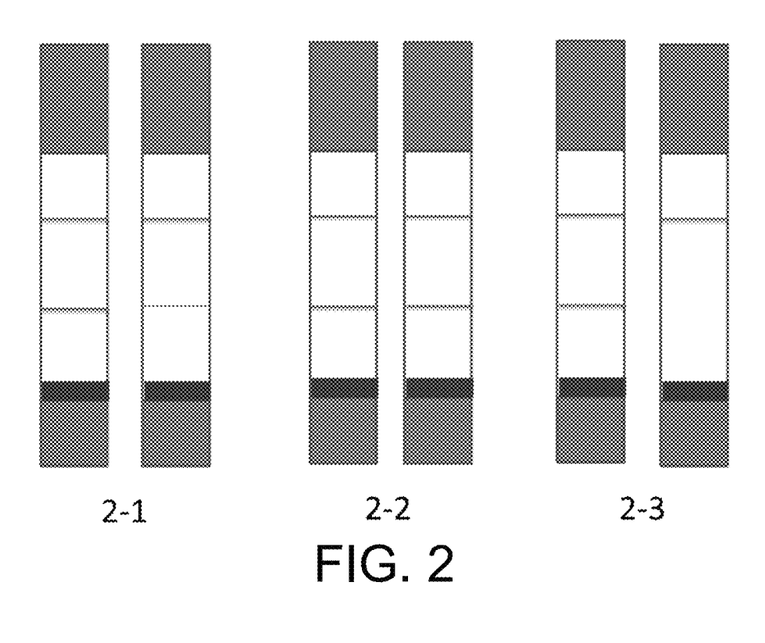
Figure 3:
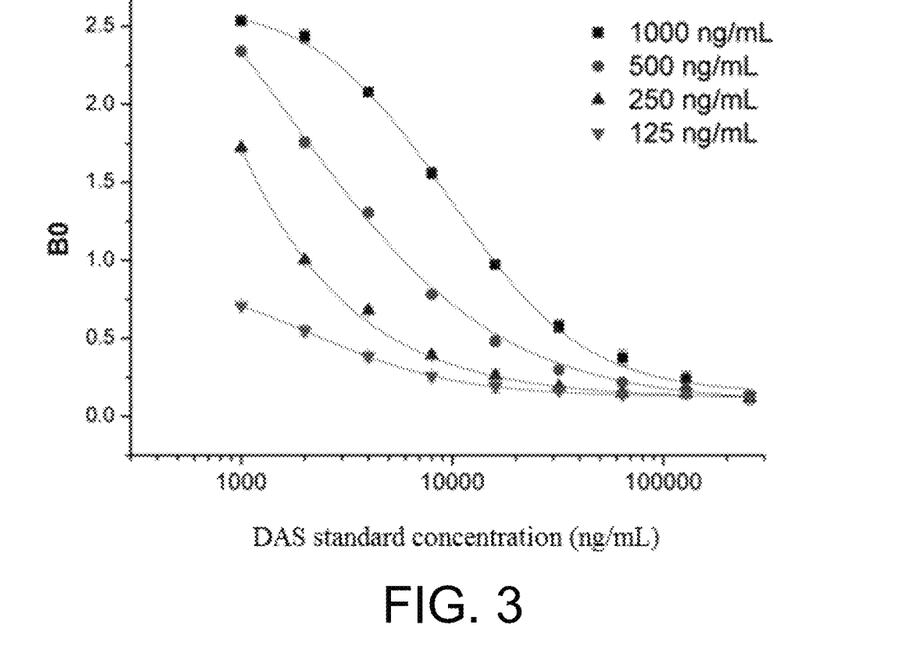
Figure 4:
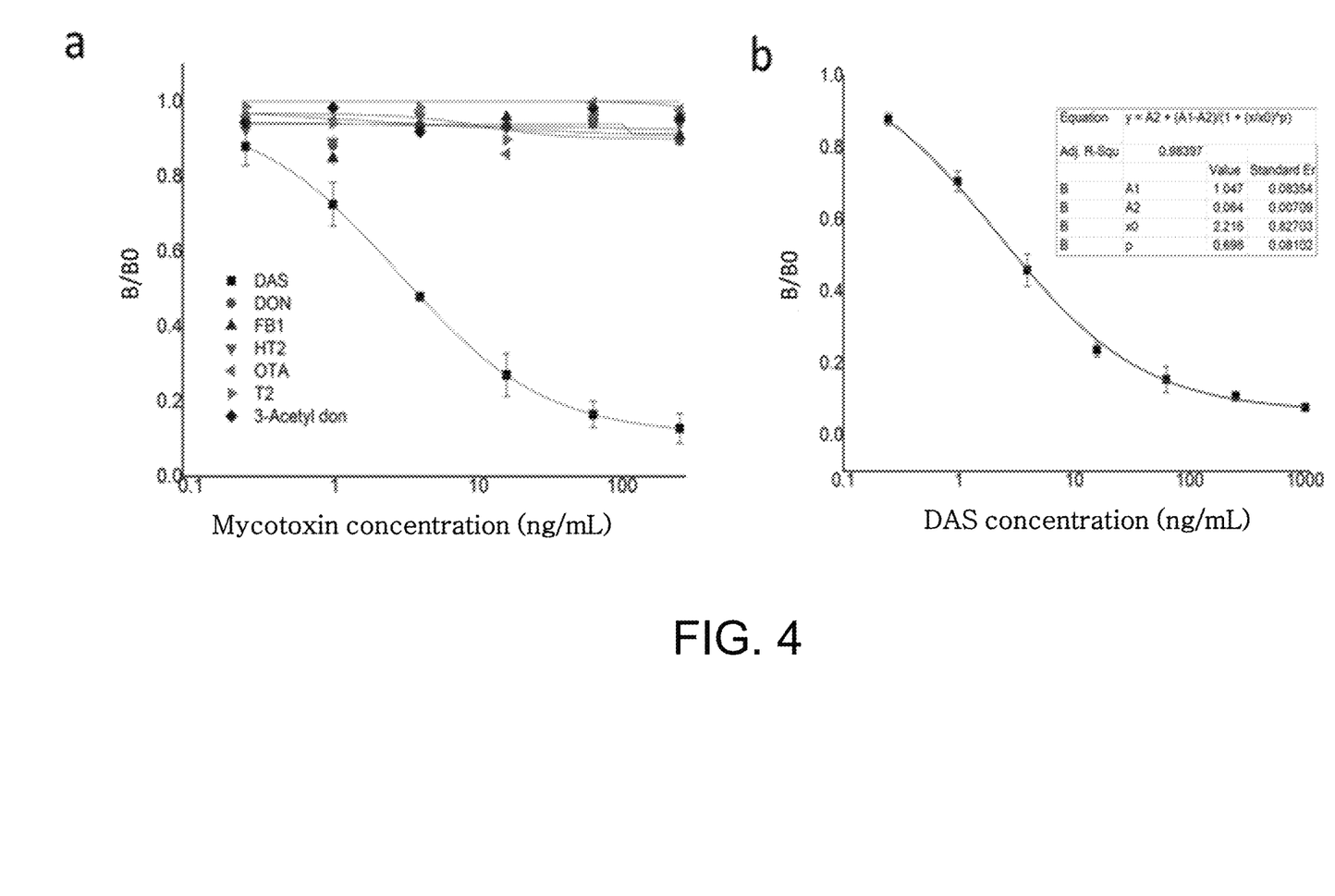

Affinity of the DAS5G11E7 was measured by using the indirect non-competitive ELISA. The ELISA plates were coated with DAS-OVA according to concentrations of 1.0 μg/mL, 0.5 μg/mL, 0.25 μg/mL, and 0.125 μg/mL, with 100 μL per pore, at 37° C. for 2 h. After blocking was performed for 1 h by using a blocking solution, the antibody diluted by PBS (a dilution factor of 1:2) was added into the ELISA plates. Other steps were the same as the indirect non-competitive ELISA. Measured OD450 values served as ordinates, and log values of antibody concentrations (mol/L) served as abscissas, to draw four S-shaped curves of four concentrations. A maximum OD value on the topmost of each S-shaped curve was found out, namely ODmax, and an antibody concentration corresponding to a 50% ODmax value of each curve was found out. Affinity constants of the antibody were calculated according to the formula Ka=(n−1)/2(n[Ab']t−[Ab]t) by grouping any two of the four concentrations into a group, where [Ab']t and [Ab]t were antibody concentrations corresponding to two 50% maximum OD values in each group, n was a multiple (including three ratios 1:2, 1:4, and 1:8) of a coated antigen concentration in each group, and six Ka values were obtained in total. The six obtained Ka values were averaged to obtain the affinity of an anti-diacetoxyscirpenol mouse ascites antibody by using the enzyme-linked immunosorbent assay (ELISA), which might reach $5.4 \times 10^8$ L/moL (FIG. 3).

Screening of Hybridoma Cell Strain DAS5G11E7

1. Animal Immunization

BALB/c mice that were six to seven weeks old were immunized by a diacetoxyscirpenol complete antigen DAS-BSA prepared in a laboratory. For the first immunization, the diacetoxyscirpenol complete antigen and an equal volume of Freund's complete adjuvant were emulsified and subcutaneously injected at multiple points in necks and backs of the mice. The second immunization was performed four weeks later. A Freund's incomplete adjuvant and an equal volume of diacetoxyscirpenol complete antigen were emulsified and injected in abdomens of the mice. The interval between the third immunization and the second immunization was 4 weeks, and the immunization manners were the same. The fourth immunization was performed 3 weeks after the third immunization, and the immunization manner was the same as that in the second immunization, that was, intraperitoneal injection. In the four immunizations, dosages were the same, that was, 70 μg for each mouse. For the first three immunizations, eight days to ten days after each immunization, blood was sampled from caudal vein, serum was separated out, and valences of the serums of the mice were measured by using the indirect ELISA. Eight days after the third immunization, tails were cut for blood sampling, and the mice corresponding to the serums with both relatively high valences and sensitivities were selected for the last enhanced immunization, with an immunization dosage twice the foregoing dosage.

2. Cell Fusion

Three days after the enhanced immunization, PEG with a weight percentage of 50% and a polyethylene glycol molecular weight of 1450 was used as a fusogen, and cell fusion was performed by using a conventional method, specifically including the steps: sacrificing the mice by cervical dislocation under aseptic conditions, taking out spleens, using a homogenizer to crush the spleens, separating out splenocytes by using a filter screen, mixing the splenocytes and murine myeloma cells SP2/0 according to a ratio of 5:1, centrifuging, resuspending mixed cells by using an RPMI-1640 basal medium, centrifuging, and discarding supernate; and adding 1 mL to 2 mL of 50% PEG within 1 min in total, adding 10 mL to 20 mL of RPMI-1640 basal medium along the wall, centrifuging, discarding supernate, resuspending fused cells at a tube bottom by using 20 mL of a cell complete medium containing 1% of HAT, adding suspended cells to 80 mL of a semi-solid medium, evenly mixing, adding the obtained mixture into a 6-pore cell culture plate, with 1.5 mL per pore, and culturing in a 37° C. carbon dioxide incubator. The cell complete medium containing 1% of HAT included: 20% (volume percentage) of fetal bovine serum, 75% (volume percentage) of RPMI-1640 basal medium, 1% (weight percentage) of L-glutamine, 1% (volume percentage) of HEPES, 1% (volume percentage) of double antibodies (10000 units per milliliter of penicillin and 10000 micrograms per milliliter of streptomycin), 2% (volume percentage) of growth factor (HFCS), and 1% (weight percentage) of hypoxanthine-aminopterin-thymidine (HAT) and methylcellulose, which was purchased from the sigma-Aldrich company.

Screening and Cloning of Cell Strain

When cell colonies grew to be visible to the naked eye two to three weeks after the cell fusion, clones were picked from the culture medium by using a micropipettor and transferred to a 96-pore cell culture plate to be cultured in HAT liquid. When cells grew to ⅔ height from the pore bottom, a culture supernate was sucked for detection. A two-step screening method was applied. In the first step, the indirect ELISA was used to screen out positive pores that were resistant to diacetoxyscirpenol other than a carrier protein BSA. In the second step, indirect competitive ELISA was used to detect the positive pores screened out in the first step, and diacetoxyscirpenol was used as a competitor to select the pores with both relatively large light absorption value and relatively high sensitivity (relatively large light absorption value meant that a final measurement value of a pore with the competitor of 0, that was, a positive control hole, was relatively large, and relatively high sensitivity meant that a competitor concentration at an inhibition ratio of 50%, that is, the IC50 value was relatively small). Subcloning was performed by using a limiting dilution method. After the subcloning, the same two-step method was used to perform detection. After subcloning was repeatedly performed for 4-5 times, the hybridoma cell strain DAS5G11E7 was obtained. This hybridoma cell strain has already been preserved on Apr. 3, 2018 in China Center For Type Culture Collection (CCTCC), the preservation address is Wuhan University, Wuhan, China, and the preservation number is CCTCC NO:C201881.

Measurement of sequences of variable regions of anti-diacetoxyscirpenol monoclonal antibody, hybridoma cell strain DAS5G11E7 antibody (1) Extraction of total RNA: a total RNA extraction kit from the Tiangen company was used to extract, following the instructions, total RNA capable of producing the hybridoma cell strain DAS5G11E7;

(2) Synthesis of cDNA: with the total RNA obtained in the step (1) as a template and oligo(dT)15 as primers, reverse transcription was performed, following the SuperScript™-2II reverse transcriptase instructions, to synthesize a first strand of cDNA; where the primers oligo(dT)15 were purchased from Invitrogen; and (3) Cloning of variable region genes by a PCR method: based on conserved sites of mouse antibody gene sequences in GENBANK, primers were designed, and the cDNA was used as a template to amplify the antibody heavy chain and light chain variable region genes. The PCR procedure included: at 94° C. for 30 s, at 58° C. for 45 s, at 72° C. for 1 min, amplification for 30 cycles, and finally elongation at 72° C. for 10 min. After electrophoretic separation was performed on the PCR product by using 1% (weight percentage) of agarose gel, DNA segments were purified and recovered by using a kit and connected into a vector pMD18-T, *Escherichia coli* DH5a competent cells were transformed, positive clones were picked and sent to Shanghai Sunny Biotechnology Co., Ltd. for sequencing. For sequences of the primers, the sequences of the heavy chain variable region primers were 5'-CAG GTS MAR CTG MAG GAG TCW G-3'(22mer) and 5'-CAG GGG CCA GTG GAT AGA CAG ATG GGGG-3'(28mer), where S, M, R, and W were degenerate bases, M=A/C, R=A/G, S=G/C, and W=A/T; and the sequences of the light chain variable region primers were 5'-GAC ATC AAG ATG ACC CAG TCT CCA-3'(24mer) and 5'-CCG TTT TAT TTC CAG CTT GGT CCC-3'(24mer).

Resulting gene sequence results: the sequence of a heavy chain variable region coding gene was 351 bp in length and was shown as SEQ ID NO:1, and it was deduced that a heavy chain variable region encoded by the gene sequence was composed of 117 amino acids and was shown as SEQ ID NO:3 based on the obtained gene sequence. The sequence of a light chain variable region coding gene was 324 bp in length and was shown as SEQ ID NO:2, and it was deduced that a light chain variable region encoded by the gene sequence was composed of 108 amino acids and was shown as SEQ ID NO:4 based on the obtained gene sequence.

Embodiment 2

A preparation method for an immunochromatography test strip for detecting pollution of diacetoxyscirpenol included the following steps:

(1) Preparation of a Water Absorption Pad

Water absorption paper was cut into a specification of 16 mm in length and 4 mm in width to obtain the water absorption pad;

(2) Preparation of a Detection Pad

A coating solution with a concentration of 0.4 mg/mL was prepared from a diacetoxyscirpenol-ovalbumin conjugate (DAS-OVA) by using a coating buffer solution. A nitrocellulose membrane was coated with the coating solution in a spot-spray manner in a position 15 mm away from an upper edge of the nitrocellulose membrane to obtain a detection line, where a coating quantity of the diacetoxyscirpenol-ovalbumin conjugate (DAS-OVA) required for each centimeter of the detection line was 150 ng. Then, drying was performed at 37° C. for 30 min.

The nitrocellulose membrane was 22 mm in length and 4 mm in width.

Coating of a Quality Control Line:

A coating solution with a concentration of 0.25 mg/mL was prepared from a rabbit antimouse polyclonal antibody by using a coating buffer solution. The nitrocellulose membrane was transversely coated with the coating solution in a position 6 mm away from the detection line in a spot-spray manner to obtain a quality control line, where a coating quantity of the rabbit antimouse polyclonal antibody required for each centimeter of the quality control line was 80 ng. Then, drying was performed at 37° C. for 1 h.

The coating buffer solution was prepared from 0.1 g of ovalbumin, 0.08 g of sodium chloride, 0.002 g of potassium chloride, 0.002 g of monopotassium phosphate, 0.029 g of sodium phosphate dibasic dodecahydrate, and water that was added until a constant volume of 10 mL.

(3) Preparation of a Sample Pad

A fiberglass membrane was cut into a specification of 12 mm in length and 4 mm in width, put into a blocking solution to be soaked, taken out, and dried at 37° C. for 8 h to obtain the sample pad. Then, the sample pad was preserved in a dryer at room temperature.

The blocking solution was prepared from 1 g of bovine serum albumin, 2 g of sucrose, 0.8 g of sodium chloride, 0.02 g of potassium chloride, 0.02 g of sodium azide, 0.02 g of monopotassium phosphate, 0.29 g of sodium phosphate dibasic dodecahydrate, and water that was added until a constant volume of 100 mL.

(4) Preparation of a Gold-Labeled Pad

A fiberglass membrane was cut into a specification of 10 mm in length and 4 mm in width, put into the blocking solution in the step (3) to be soaked, taken out, and dried at 37° C. for 8 h. The dried fiberglass membrane was transversely spray-coated with a nanogold-labeled anti-diacetoxyscirpenol monoclonal antibody solution in a spot-spray manner, where a dosage of a nanogold-labeled anti-diacetoxyscirpenol monoclonal antibody required for each centimeter of spray-coating length was 125 ng. Then, vacuum freeze-drying was performed for 2 h, and the gold-labeled pad was preserved in a dryer at room temperature.

The nanogold-labeled anti-diacetoxyscirpenol monoclonal antibody solution was prepared by using an unsaturated labeling method, specifically including: taking 50.0 mL of a commercially available nanogold solution with a mass concentration of 0.01%, adjusting a pH value by using 0.4 mL of a 0.1 mol/L potassium carbonate aqueous solution, slowly adding 2 mL of a 0.1 mg/mL anti-diacetoxyscirpenol monoclonal antibody aqueous solution while stirring, and continuing conducting stirring for 30 min; adding a bovine serum albumin aqueous solution with a mass concentration of 10% until a final mass concentration of bovine serum albumin is 1%, and continuing conducting stirring for 30 min; standing at 4° C. for 2 h, centrifuging at 1500 r/min for 15 min, taking the obtained supernate, and discarding the obtained precipitate; centrifuging the supernate at 12000 r/min for 30 min, discarding the obtained supernate, and adding 40.0 mL of label washing preserving fluid; and then, centrifuging at 12000 r/min for 30 min, discarding the obtained supernate, resuspending the obtained precipitate by using label washing preserving fluid to obtain 5.0 mL of a concentrate, and placing in a refrigerator at 4° C. for standby application; where a mass concentration of the nanogold-labeled anti-diacetoxyscirpenol monoclonal antibody solution was 0.06 mg/mL;

a particle size of nanogold in the nanogold solution was 15 nm;

the 0.1 mol/L potassium carbonate aqueous solution was prepared by dissolving 13.8 g of potassium carbonate in pure water until a constant volume of 1000 mL and filtering by using a 0.22 μm filter membrane; and the label washing preserving fluid was prepared from 0.1235 g of boric acid, 0.2 g of sodium azide, 2.0 g of polyethylene glycol-20000 and pure water in a constant volume of 1000 mL by filtering by using a 0.22 μm filter membrane.

(5) Assembling of a Test Strip

The water absorption pad, the detection pad, the gold-labeled pad, and the sample pad overlapped by 1 mm to 3 mm at joints and were sequentially attached to one side of a paper board. The detection pad used the nitrocellulose membrane as a base pad and was transversely coated with the detection line and the quality control line, as shown in FIG. 1.

Application of the immunochromatography test strip for detecting pollution of diacetoxyscirpenol to detecting a wheat flour sample included:

weighing 20 g of wheat flour sample, adding 100 mL of a methanol aqueous solution with a volume concentration of 70%, evenly mixing, ultrasonically extracting in a water bath at 50° C. for 10 min, standing for 10 min, filtering the supernate, namely the obtained extract by using a 0.45 μm organic filter membrane, taking 100 μL of to-be-tested sample solution as a detected solution to be dropwise added onto the sample pad of the immunochromatography test strip for detecting pollution of diacetoxyscirpenol as a detection test strip, taking 100 μL of methanol aqueous solution with a methanol concentration of 14% as a negative control solution to be dropwise added onto a sample pad of another immunochromatography test strip as a control test strip, and reading results 15 min later.

Detection Results:

A red stripe was shown on a quality control line of the detection test strip for the 1# to-be-tested sample and color of a detection line was lighter than color of a detection line of the control test strip, as shown in FIG. 2-1, it was determined that a quantity of diacetoxyscirpenol contained in the 1# to-be-tested sample solution was equal to or higher than 5 ng/mL and less than 100 ng/mL and might be converted into a quantity of diacetoxyscirpenol contained in the 1# to-be-tested sample, which was equal to or higher than 25 ng/g and less than 500 ng/g.

A red stripe was shown on a quality control line of the detection test strip for the 2# to-be-tested sample and color of a detection line approached color of a detection line of the control test strip, as shown in FIG. 2-2, it was determined that a quantity of diacetoxyscirpenol contained in the 2# to-be-tested sample solution was less than 5 ng/mL and might be converted into a quantity of diacetoxyscirpenol contained in the 2# to-be-tested sample, which was less than 25 ng/g.

A red stripe was shown on a quality control line of the detection test strip for the 3# to-be-tested sample and color was not developed on a detection line, as shown in FIG. 2-3, it was determined that a quantity of diacetoxyscirpenol contained in the 3# to-be-tested sample solution was equal to or higher than 100 ng/mL and might be converted into a quantity of diacetoxyscirpenol contained in the 3# to-be-tested sample, which was equal to or higher than 500 ng/g.

What is claimed is:

1. An immunochromatography test strip for detecting pollution of diacetoxyscirpenol, comprising a bottom plate, wherein a water absorption pad, a detection pad, a gold-labeled pad and a sample pad are sequentially attached to one side of the bottom plate from top to bottom, adjacent pads are connected in an overlapping manner at a joint, the detection pad uses a nitrocellulose membrane as a base pad, a transverse quality control line and a detection line are arranged on the nitrocellulose membrane, the quality control line is coated with a rabbit antimouse polyclonal antibody, the detection line is located below the quality control line, and the detection line is coated with a diacetoxyscirpenol-ovalbumin conjugate; the gold-labeled pad is transversely spray-coated with a nanogold-labeled anti-diacetoxyscirpenol monoclonal antibody; and the anti-diacetoxyscirpenol monoclonal antibody is secreted by a hybridoma cell strain DAS5G11E7 with the preservation number of CCTCC NO.C201881.

2. The immunochromatography test strip for detecting pollution of diacetoxyscirpenol according to claim 1, wherein the water absorption pad is 16 mm to 18 mm in length and 3 mm to 4 mm in width, the detection pad is 18 mm to 30 mm in length and 3 mm to 4 mm in width, the gold-labeled pad is 10 mm to 12 mm in length and 3 mm to 4 mm in width, the sample pad is 12 mm to 15 mm in length and 3 mm to 4 mm in width, and an overlapping length of adjacent pads is 1 mm to 3 mm.

3. The immunochromatography test strip for detecting pollution of diacetoxyscirpenol according to claim 1, wherein a distance between the detection line and an upper edge of the nitrocellulose membrane is 15 mm to 20 mm, and a distance between the detection line and the quality control line is 5 mm to 7 mm.

4. The immunochromatography test strip for detecting pollution of diacetoxyscirpenol according to claim 1, wherein a coating quantity of the diacetoxyscirpenol-ovalbumin conjugate required for each centimeter of the detection line is 100 ng to 300 ng, and a coating quantity of the rabbit antimouse polyclonal antibody required for each centimeter of the quality control line is 50 ng to 200 ng.

5. The immunochromatography test strip for detecting pollution of diacetoxyscirpenol according to claim 1, wherein a particle size of nanogold used in the gold-labeled pad is 15 nm to 20 nm, and a dosage of the nanogold-labeled anti-diacetoxyscirpenol monoclonal antibody required for each centimeter of spray-coating length on the gold-labeled pad is 100 ng to 200 ng.

6. A preparation method for the immunochromatography test strip for detecting pollution of diacetoxyscirpenol according to claim 1, comprising the following steps:

(1) preparation of the water absorption pad cutting water absorption paper to obtain the water absorption pad;

(2) preparation of the detection pad coating of the detection line:

preparing a coating solution with a concentration of 0.25 mg/mL to 0.5 mg/mL from the diacetoxyscirpenol-ovalbumin conjugate by using a coating buffer solution, coating the nitrocellulose membrane with the coating solution in a spot-spray manner to obtain the detection line, and then drying at 37° C. to 40° C. for 30 min to 60 min;

wherein a coating quantity of the diacetoxyscirpenol-ovalbumin conjugate required for each centimeter of the detection line coated with the diacetoxyscirpenol-ovalbumin conjugate is 100 ng to 300 ng, and a distance between the detection line and an upper edge of the nitrocellulose membrane is 15 mm to 20 mm;

coating of the quality control line:

preparing a coating solution with a concentration of 0.2 mg/mL to 0.4 mg/mL from the rabbit antimouse polyclonal antibody by using a coating buffer solution; transversely coating the nitrocellulose membrane with the coating solution in a position 5 mm to 7 mm away from the detection line close to the quality control line in a spot-spray manner to obtain the quality control line, wherein a coating quantity of the rabbit antimouse polyclonal antibody required for each centimeter of the quality control line is 50 ng to 200 ng; and then, drying at 37° C. to 40° C. for 1 h to 2 h;

(3) preparation of the sample pad:

putting a fiberglass membrane into a blocking solution to be soaked, taking out the soaked fiberglass membrane, and drying at 37° C. to 40° C. for 6 h to 10 h to obtain the sample pad, and then, preserving the sample pad in a dryer at room temperature;

(4) preparation of the gold-labeled pad putting a fiberglass membrane into a blocking solution to be soaked, taking out the soaked fiberglass membrane, and drying at 37° C. to 40° C. for 6 h to 10 h; transversely spray-coating the dried fiberglass membrane with a nanogold-labeled anti-diacetoxyscirpenol monoclonal antibody solution in a spot-spray manner, wherein a dosage of the nanogold-labeled anti-diacetoxyscirpenol monoclonal antibody required for each centimeter of spray-coating length is 100 ng to 200 ng; and then, vacuum freeze-drying for 2 h to 4 h, and preserving in a dryer at room temperature; wherein the anti-diacetoxyscirpenol monoclonal antibody is secreted by a hybridoma cell strain DAS5G11E7 with the preservation number of CCTCC NO.C201881; and (5) assembling of the test strip sequentially attaching the water absorption pad, the detection pad, the gold-labeled pad and the sample pad to one side of a bottom plate from top to bottom to obtain the immunochromatography test strip for detecting pollution of diacetoxyscirpenol, wherein adjacent pads are connected in an overlapping manner at a joint, and an overlapping length is 1 mm to 3 mm.

7. The preparation method for the immunochromatography test strip for detecting pollution of diacetoxyscirpenol according to claim 6, wherein the coating buffer solution comprises in each 10 mL: 0.08 g of sodium chloride, 0.002 g of potassium chloride, 0.002 g of monopotassium phosphate, 0.1 g to 0.2 g of ovalbumin, and 0.029 g of sodium phosphate dibasic dodecahydrate.

8. The preparation method for the immunochromatography test strip for detecting pollution of diacetoxyscirpenol according to claim 6, wherein the blocking solution used in the step (3) and the step (4) comprises in each 100 mL: 2 g to 5 g of sucrose, 0.8 g of sodium chloride, 0.02 g of potassium chloride, 0.02 g to 0.05 g of sodium azide, 0.02 g of monopotassium phosphate, 1 g to 2 g of bovine serum albumin, and 0.29 g of sodium phosphate dibasic dodecahydrate.

9. The preparation method for the immunochromatography test strip for detecting pollution of diacetoxyscirpenol according to claim 6, wherein the nanogold-labeled anti-diacetoxyscirpenol monoclonal antibody is prepared by using an unsaturated labeling method, specifically comprising: taking 50.0 mL of a commercially available nanogold solution with a mass concentration of 0.01%, adjusting a pH value by using 0.6 mL of a 0.1 mol/L potassium carbonate aqueous solution, slowly adding 2.0 mL of a 0.1 mg/mL anti-diacetoxyscirpenol monoclonal antibody aqueous solution while stirring, and continuing conducting stirring for 30 min; adding a bovine serum albumin aqueous solution with a mass concentration of 10% until a final mass concentration of bovine serum albumin is 1%, and continuing conducting stirring for 30 min; standing at 4° C. for 2 h, centrifuging at 1500 r/min for 15 min, taking the obtained supernate, and discarding the obtained precipitate; centrifuging the supernate at 12000 r/min for 30 min, discarding the obtained supernate, and adding 40.0 mL of label washing preserving fluid; and then, centrifuging at 12000 r/min for 30 min, discarding the obtained supernate, resuspending the obtained precipitate by using label washing preserving fluid to obtain 5.0 mL of a concentrate, and placing the obtained concentrate in a refrigerator at 4° C. for standby application;

wherein the 0.1 mol/L potassium carbonate aqueous solution is prepared by dissolving 13.8 g of potassium carbonate in pure water until a constant volume of 1000 mL and filtering by using a 0.22 μm filter membrane, and the label washing preserving fluid is prepared from 0.2 g of sodium azide, 0.1235 g of boric acid, 2.0 g of polyethylene glycol-20000 and pure water in a constant volume of 1000 mL by filtering by using a 0.22 μm filter membrane.

10. Application of the immunochromatography test strip for detecting pollution of diacetoxyscirpenol according to claim 1, wherein its application method-comprising: weighing a to-be-tested ground sample, adding a methanol aqueous solution with a volume concentration of 60% to 80%, evenly mixing, ultrasonically extracting in a water bath at 50° C. to 60° C. for 5 min to 10 min, standing for 5 min to 10 min, diluting the obtained supernate, namely the obtained extract with water so that a final volume concentration of methanol in diluted liquid is 20% to 30% to obtain a to-be-tested sample solution, taking 80 μL to 150 μL of the to-be-tested sample solution as a detected solution to be dropwise added onto the sample pad of the immunochromatography test strip for detecting pollution of diacetoxyscirpenol for detection as an a detection test strip, taking an equal volume of methanol aqueous solution with a consistent methanol concentration as a negative control solution to be dropwise added onto a sample pad of another immunochromatography test strip for detecting pollution of diacetoxyscirpenol as a control test strip, and performing developing contrast on the detection test strip and the control test strip 15 min to 20 min later, wherein when color of the detection line coated with the diacetoxyscirpenol-ovalbumin conjugate on the detection test strip approaches color of the corresponding detection line on the control test strip, it is indicated that a quantity of diacetoxyscirpenol contained in the to-be-tested sample solution is less than 5 ng/mL; when the color of the detection line coated with the diacetoxyscirpenol-ovalbumin conjugate on the detection test strip is lighter than the color of the corresponding detection line on the control test strip, it is indicated that a quantity of diacetoxyscirpenol contained in the to-be-tested sample solution is equal to or higher than 5 ng/mL and less than 100 ng/mL; when color is not developed, it is indicated that a quality of diacetoxyscirpenol contained in the to-be-tested sample solution is equal to or higher than 100 ng/mL; and when color is not developed on the quality control line, the test strip is determined as invalid no matter whether color is developed on the detection line of the detection test strip; and finally, a quantity of diacetoxyscirpenol contained in the to-be-tested sample is obtained through conversion.

* * * * *